United States Patent [19]

Dickerson et al.

[11] Patent Number: 4,986,263

[45] Date of Patent: Jan. 22, 1991

[54] MUSCULOSKELETAL KNEE SUPPORT

[75] Inventors: Jeffrey P. Dickerson, Warsaw; Scott Charlton, Silver Lake, both of Ind.

[73] Assignee: Biomet, Inc., Warsaw, Ind.

[21] Appl. No.: 512,858

[22] Filed: Apr. 23, 1990

[51] Int. Cl.$^5$ .......................... A61F 3/00; A61F 5/00
[52] U.S. Cl. ................ 128/80 C; 128/80 R; 2/22; 2/24
[58] Field of Search ............... 128/80 C, 80 R, 89 R; 2/22, 24

[56] References Cited

U.S. PATENT DOCUMENTS

| | | | |
|---|---|---|---|
| 3,934,583 | 1/1976 | Hollingshead et al. | 128/80 C X |
| 4,084,584 | 4/1978 | Detty | 128/80 C |
| 4,084,586 | 4/1978 | Hettick | 128/80 C X |
| 4,445,505 | 5/1984 | Labour et al. | 128/80 C |
| 4,724,831 | 2/1988 | Huntjens | 128/80 C |

*Primary Examiner*—Richard J. Apley
*Assistant Examiner*—Jennifer L. Doyle
*Attorney, Agent, or Firm*—Ice Miller Donadio & Ryan

[57] ABSTRACT

An anatomical musculoskeletal therapeutic knee sleeve support especially adapted to be placed over the knee to provide support for the muscles and skeletal structure of the knee during physical activity, particularly sports activity. The sleeve comprises a single panel of flexible resilient material cut and joined in such a manner that there is a stitched seam at the upper half of the sleeve on one side of the knee posterior to the side of the knee and another stitched seam at the lower half of the sleeve on the other side of the knee posterior of the side of the knee and an open horizontal aperture at the rear flexure point of the knee between central points of the stitched seams.

15 Claims, 3 Drawing Sheets

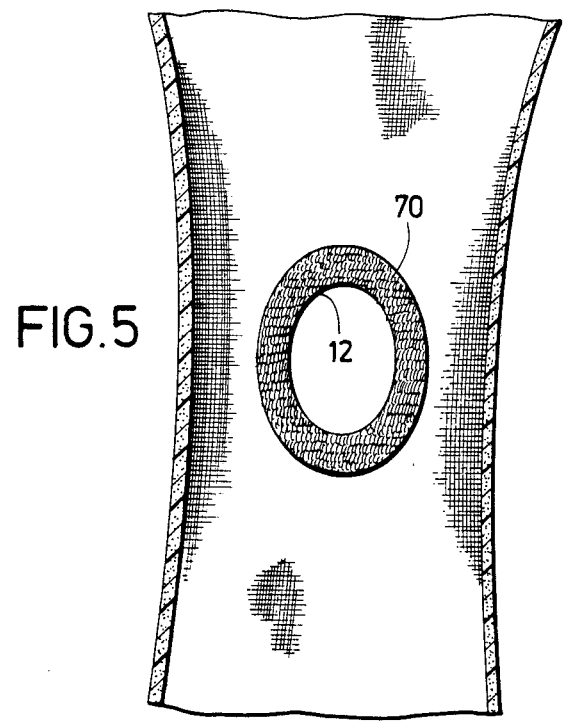
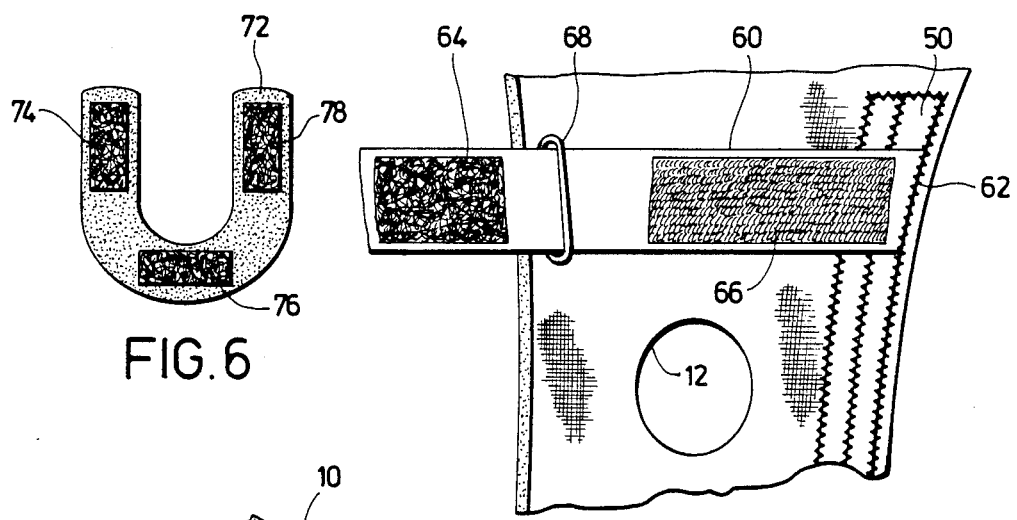
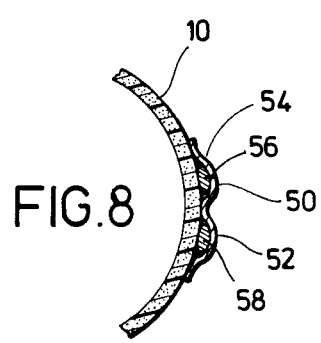

MUSCULOSKELETAL KNEE SUPPORT

BACKGROUND OF THE INVENTION

This invention relates to a musculoskeletal knee support and more particularly for a therapeutic anatomical support of the type used to apply pressure around the knee to provide protection and support during physical activity, particularly sports activity.

Various devices have previously been developed to provide therapeutic support to the knee during normal knee movements such as during walking, running or athletic activity. Typically, such supports are used to provide additional support for an injured knee so that the wearer can continue physical activity despite the injury. Various prior art devices are typically represented by those disclosed in U.S. Pat. No. 3,934,583—Hollingshead et al. and U.S. Pat. No. 4,084,584—Detty.

The present invention has been developed to obviate some of the deficiencies in the prior art. For example, U.S. Pat. No. 4,084,584—Detty comprises two separate pieces of material joined together along two substantially parallel seams. This two piece construction requires additional and unnecessary cutting and stitching operations during manufacture and multiple sized patterns for the two pieces for different sized knees. Accordingly, there is an increased risk that pattern sizes or cut pieces will get mixed up, resulting in the wrong sized pieces being stitched together during manufacture. For example, with the prior art two piece construction, if a small back panel is accidentally stitched to a large front panel, the resulting sleeve will be a manufacturing reject.

U.S. Pat. No. 3,934,583—Hollingshead comprises a single piece construction which avoids the problems with the multi-piece construction discussed above. However, the Hollingshead sleeve is constructed so that it has a single seam down the back of the knee which causes irritation problems for the user. Because of the way the knee flexes, it is desirable to have the seam of such a support sleeve at the posterior of each side of the knee slightly behind the line of the fibular collateral ligament and the tibial collateral ligament.

The present invention obviates the deficiencies of the prior art by providing a unitary, single piece construction, but which positions the seam of the sleeve along the posterior of the side of the knee where it minimizes the irritation problems of single seam construction.

A further deficiency of the prior art has been irritation caused at the back of the knee along the fold line of the skin. To alleviate this problem, it has been found advantageous to place a horizontal aperture in the sleeve at the skin fold line at the back of the knee.

Another deficiency in the prior art has been in providing proper support for the patella. Certain injuries to the knee can result in the patella shifting during physical activity, thereby increasing the possibility of dislocation or further injury. The prior art sleeves, while recognizing the problem, have not provided an adjustable patella support that permits a variation in the position of the support to assure that the patella remains in the proper position during physical activity.

BRIEF SUMMARY OF THE INVENTION

A musculoskeletal knee support adapted to be placed over the human knee to support the knee during physical activity in accordance with the present invention comprises a multiple edge single piece of resilient flexible material having an top edge and a bottom edge being essentially parallel to one another. The single piece of material also has opposing upper edges and opposing lower edges angularly disposed with respect to the top and bottom edges. The opposing upper edges are laterally separated from the opposing lower edges by essentially horizontal edges. The single piece of material is formed into a generally cylindrical sleeve conforming generally to the shape of the knee and the lower thigh and upper calf adjacent the knee. The sleeve also has a first stitched seam on one side of the upper half of the posterior side of the knee along said upper opposing edges and a second stitched seam on the other side of the lower half of the posterior side of the knee along said lower opposing edges. A generally horizontal aperture is formed between said horizontal edges positioned at the rear fold line of the skin at the back of the knee opposite said opening for the patella. Typically, the first and second stitched seams are respectively positioned approximately along the line of the fibular collateral ligament and the tibular collateral ligament to reduce irritation.

The sleeve may have an opening positioned to receive and permit the patella of the knee to project therethrough. A patella retaining means may be positioned around a portion of the patella opening to help retain said patella in a desired position. The patella retaining means may be adjustable so that it can be located at a different position around said opening to provide patella support in any desired direction. Further, first disengagable fastening means may be positioned around said opening, and second disengagable fastening means attached to the patella retaining means for engaging said first fastening means so that the patella retaining means can be disengaged and moved to any desired location around the opening.

The flexible resilient material from which the support is fabricated may be an elastomeric foam backed with cloth fiber. Neoprene has been found to be particularly suitable.

Tightening means may be provided adjacent said top and bottom edges of the sleeve for adjustably tightening upper and lower portions of said sleeve after said sleeve is placed over the knee.

Additionally, the sleeve may have stiffening means attached approximately along a vertical medial line at each side of the knee to aid in lateral support of the knee.

Accordingly, it is a principal object of this invention to provide a novel musculoskeletal knee support of unitary, single piece construction that obviates the deficiencies of the prior art.

It is a further object of the present invention to provide a musculoskeletal knee support particularly adapted to retain the patella of the knee in a desired position during physical activity.

It is yet a further object of the present invention to provide a musculoskeletal knee support having adjustable means for supporting the patella so that patella support can be adapted and adjusted for each particular user of the support.

It is yet a further objective of the present invention to provide a knee support that substantially eliminates seam irritation to the skin of the user.

These and other objects, advantages and features of the present invention shall hereinafter appear in the preferred embodiment which is described for the purpose of illustration and not for the purpose of limiting the breadth and scope of the present invention.

BRIEF DESCRIPTION OF THE DRAWINGS

FIG. 5 is a cross-sectional view taken substantially along the line of 5—5 in FIG. 3 showing the interior of the front portion of the knee support of the preferred embodiment.

FIG. 6 is an illustration of the adjustable patella support member in accordance with the preferred embodiment of the present invention.

FIG. 7 is a front partially fragmentary view of the preferred embodiment of the present invention showing a tightening strap after being disengaged.

FIG. 8 is a cross-sectional view taken substantially along line 8—8 in FIG. 3.

DETAILED DESCRIPTION OF THE PREFERRED EMBODIMENT

Figure 1:
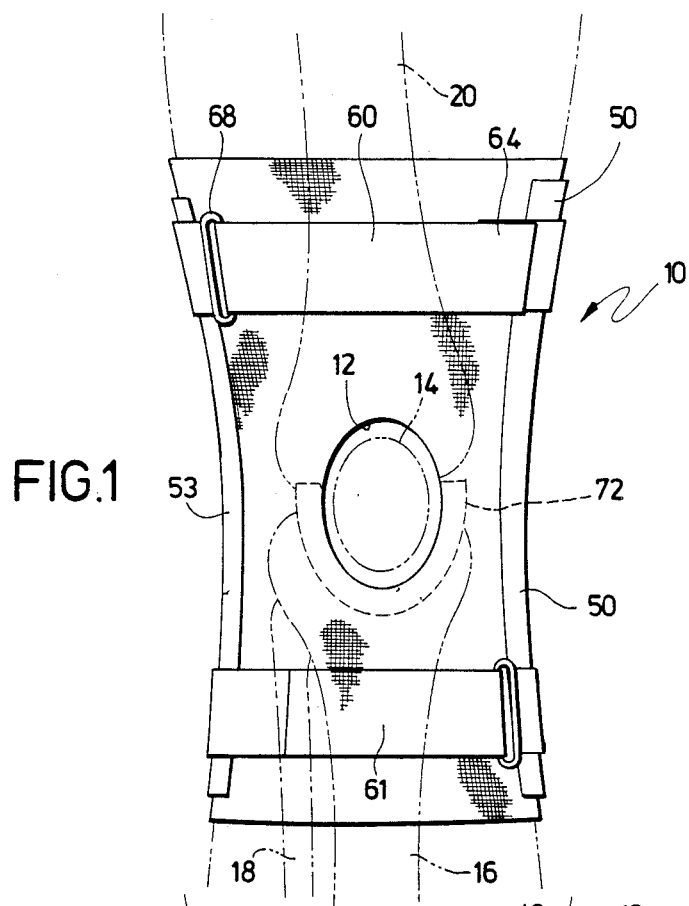
FIG. 1 is a front view of a preferred embodiment of the present invention being in position over a human knee (shown in dotted lines).
Figure 2:
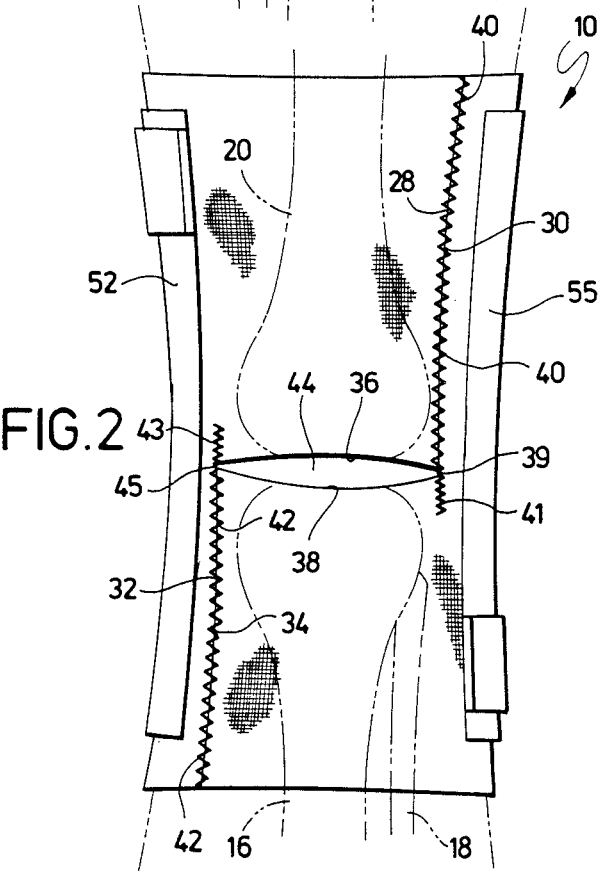
FIG. 2 is a rear view of the embodiment illustrated in FIG. 1.
Figure 3:
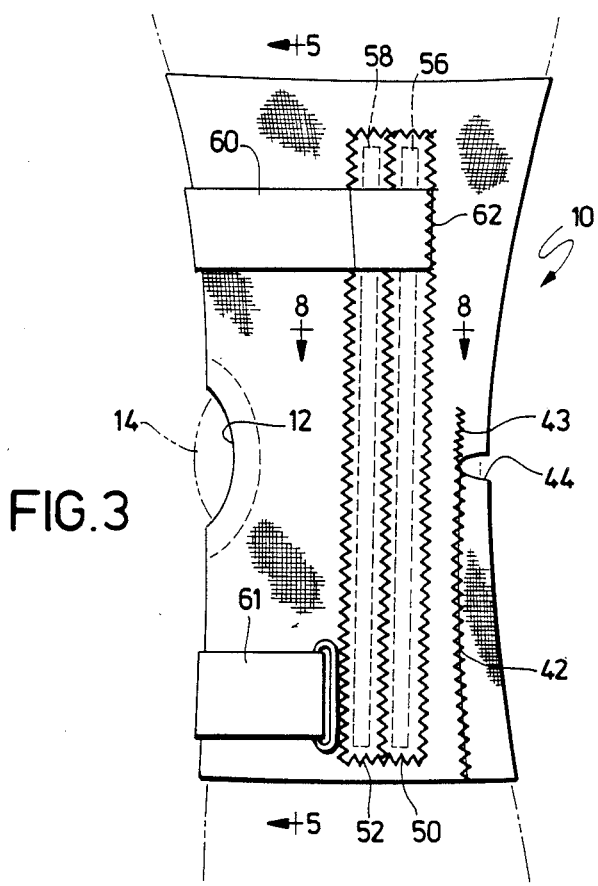
FIG. 3 is a side view of the embodiment illustrated in FIG. 1.

With reference to FIGS. 1, 2 and 3, musculoskeletal support comprises substantially cylindrical sleeve 10 formed of a flexible resilient material, preferably an elastomeric foam backed with cloth such as a neoprene fabric backed material. However, other flexible resilient materials may also be suitable.

An opening 12 is provided in the front of the sleeve 10 to receive the patella 14 of the knee (shown in dotted lines). The other bones of the knee, the tibia 16, the fibula 18 and the femur 20, are also generally indicated by dotted lines.

Figure 4:
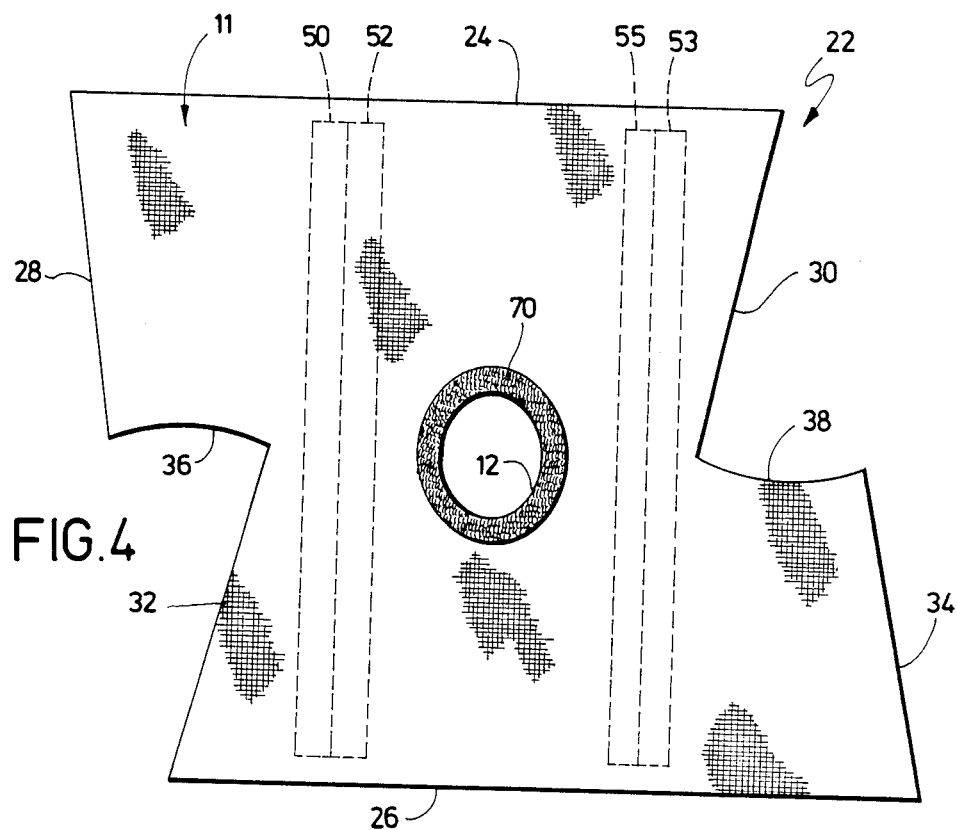
FIG. 4 is an illustration of the configuration of an open piece of material used for construction of the single piece knee support in accordance with the preferred embodiment of the present invention, illustrated in FIGS. 1, 2 and 3.

With reference to FIGS. 2 and 4, sleeve 10 is fabricated from a single piece 11 of flexible resilient material cut to have a top edge 24 and a bottom edge 26 approximately parallel to one another. Piece 11 also has upper opposing edges 28 and 30 and lower opposing edges 32 and 34 disposed at a slight angle with respect to top edge 24 and bottom edge 26 so that when formed into a cylindrical sleeve, the sleeve is tapered to more closely conform to the shape of the knee, the lower thigh and upper calf. The upper opposing edges 28 and 30 and lower opposing edges 32 and 34 are laterally separated from one another by essentially horizontal edges 36 and 38. Horizontal edges 36 and 38 are curved slightly in a concave fashion for the purpose of forming an aperture as shall be hereinafter more fully described.

With reference to FIG. 2, edge 28 is folded around until it is immediately opposite edge 30 and the two upper opposing edges are stitched together by stitches 40. Stitches 41 extend about one inch beyond the end of stitches 40 at the junction of horizontal edges 36 and 38 to reinforce the corner 39 of aperture 44. Similarly, lower opposing edge 34 is folded around until it is immediately opposite edge 32 and the two lower opposing edges are stitched together by stitches 42. Stitches 43 extend about one inch beyond the end of stitches 42 at the junction of horizontal edges 36 and 38 to reinforce corner 45 of aperture 44. In this manner, a unitary essentially cylindrical sleeve 10 is formed.

Horizontal edges 36 and 38 are not stitched together so that an open elliptical aperture 44 is formed between edges 36 and 38. Aperture 44 is positioned so that it falls approximately at the fold line of the skin at the back of the knee and permits the knee to flex readily without the sleeve 10 bunching at the fold line thereby reducing the possibility of irritation at that point. Further, by moving the stitches 40 and 42 away from the back of the knee and placing the stitches along the posterior edge of each side of the knee, slightly behind the line of the fibular collateral ligament and the tibial collateral ligament, irritation or discomfort from the stitching is virtually eliminated.

Horizontal edges 36 and 38 are slightly curved away from each other to expand the opening in aperture 44. By properly selecting the amount of curvature, an elliptical aperture 44 may be formed which permits full flexure of the knee without the edges 36 and 38 bunching and causing irritation at the back of the knee but without detracting from or reducing the support provided by the sleeve, particularly around the patella. It has been found that the vertical width of the aperture should not exceed about one and one half inches or the support at the front of the sleeve is reduced. Further, the aperture should not be less than about one quarter inch or irritation may result.

With reference to FIG. 3, positioned along each side of the sleeve approximately along the vertical medial axis through the pivot point of the knee are stiffeners 50, 52, 53 and 55. With reference to FIG. 8, stiffeners 50 and 52 comprise a single piece of material 54 overlying and stitched to retain flexible members 56 and 58 which extend substantially along the length of the sleeve 10. Members 56 and 58 provide additional lateral support for the knee during physical activity and are formed of a material that is more ridged than the material of sleeve 10 but sufficiently flexible to permit the knee to flex. Members 56 and 58 may be fabricated from rubber, plastic, stainless spring steel or other suitable material that will permit flex but also provide adequate support.

With reference to FIGS. 1, 3, and 7, tightening strap 60 is connected by stitches 62 along the stitched edge of stiffener 50. Strap 60 is an elongated rectangular piece of fabric material having velcro type fastening means attached at 64 and at 66. Strap 60 is threaded through a flattened eyelet 68 which is attached along a seam of stiffening means 53 on the opposite side of sleeve 10 from stiffening means 50 and 52. After sleeve 10 is placed over the knee, strap 60 is pulled through eyelet 68, folded over tightly and velcro type fastening means 64 is placed in contract with velcro type fastening mean 66 to attach the ends of the strap together to hold the sleeve firmly in place at the top of the knee. A similar tightening strap 61 of comparable construction is placed at the lower portion of sleeve 10 to similarly tighten the sleeve around the lower portion of the knee.

With reference to FIGS. 4 and 5, positioned and stitched around the interior of patella opening 12 is a ring of velcro type fastening means 70. With reference to FIG. 6, patella retaining member 72 is formed in an essentially C or horse shoe shape from a firm but resilient material such as felt. Velcro type fastening means 74, 76 and 78 are stitched at various points around member 72. Patella retaining member 72 may be positioned around opening 12 and affixed by the velcro type fastening means 70, 74, 76 and 78 as is illustrated by the dotted lines in FIG. 1. Further, patella retaining member 72 can be rotated around opening 12 and affixed s that it provides patella support either from the bottom, top, side or any angle. This flexibility is particularly advantageous since the nature of the injury often determines the direction needed for patella support for the user of the sleeve.

The present invention provides numerous advantages over the construction of the prior art. The single piece unitary construction of the present invention as illustrated in FIG. 4 is particularly advantageous since only one pattern is needed per sleeve size and it is impossible to mix up multiple sized pieces during the manufacturing and stitching of the knee sleeve. The multi-piece construction of the prior art requires more individual cutting operations, increasing manufacturing costs and the likelihood of manufacturing reject through misjoining inappropriately sized pieces.

An additional advantage of the present invention results from the placement of the seam. As illustrated in FIG. 2, by placing the stitched seams 40 and 42 along the posterior edge of the side of the knee, away from the flexure point of the skin fold line at the back of the knee, skin irritation of the user due to the stitching is substantially eliminated since the stitching remains in a relatively fixed position with respect to the skin along this point of the knee. The stitches 40 and 42 are designed to fall approximately along a line slightly behind the line of the fibular collateral ligament and the tibular collateral ligament since this position reduces the possibility of skin irritation.

Further, constructions that do not provide an aperture 44 at the rear of the knee increase the likelihood of irritation and discomfort from material bunching at that point. Without an aperture 44, the material tends to be compressed when the knee is fully flexed causing the material to bunch into a compressed fold along the fold line of the skin at the back of the knee. After prolonged used, the constant bunching and unbunching of the material can result in irritation at the back of the knee. However, with the construction of the present invention, the elongated aperture 44 eliminates the bunching and irritation problem. Additionally, by providing an elongated elliptical aperture, the sleeve provides firm compressive support around patella opening 12. It has been found that the single piece construction of the recent invention permits use of a rear aperture 44 without reducing the patella support provided by opening 12 and patella retaining member 72.

Further, the tightening straps of the present invention permit the sleeve to be firmly anchored both above and below the knee to minimize shifting during use and maximize support. This positive locking by the tightening straps 60 and 61 provides definite advantages over the construction of the prior art.

Another advantageous feature of the present invention is the adjustable patella positioning member 72. Since member 72 is detachable and rotatable about opening 12 to any desired position, the user can change the position to any desired position providing maximum support and comfort. Further, since member 72 is fabricated from a resilient material such as felt, it can be trimmed with scissors to a desired shape less than the full "C" shown in FIG. 6.

Stiffeners 50 and 52 also are desirable features of the present invention since they provide lateral support above and beyond the support provided by the flexible neoprene material from which the sleeve 10 is typically fabricated.

It should be recognized that various changes, alterations and modifications of the preferred embodiment may be made without departing from the spirit and scope of the present invention as claimed in the appended claims

We claim:

1. A musculoskeletal knee support adapted to be placed over the human knee to support the knee during physical activity comprising:

a multiple edge single piece of resilient flexible material having an top edge and a bottom edge being essentially parallel to one another, opposing upper edges and opposing lower edges angularly disposed with respect to said top and bottom edges, said opposing upper edges being laterally separated from said opposing lower edges by essentially horizontal edges, said single piece of material being formed into a generally cylindrical sleeve conforming generally to the shape of the knee and the lower thigh and upper calf adjacent the knee, said sleeve having a first stitched seam along said upper opposing edges at the upper half of said sleeve posterior to one side of the knee and a second stitched seam along said lower opposing edges at the lower half of the sleeve posterior of the other side of the knee and with a generally horizontal aperture between said horizontal edges positioned at the rear fold line of the skin at the back o the knee.

2. A musculoskeletal knee support as claimed in claim 1 wherein said sleeve has a opening positioned to receive and permit the patella of the knee to project therethrough opposite said generally horizontal aperture.

3. A musculoskeletal knee support as claimed in claim 2, wherein said sleeve has a patella retaining means positioned around a portion of said opening to help retain said patella in a desired position.

4. A musculoskeletal knee support as claimed in claim 3, wherein said patella retaining means is disengagable so that it can be moved to a different position around said opening to provide patella support in any desired direction.

5. A musculoskeletal knee support as claimed in claim 3 wherein first disengagable fastening means is positioned around said opening, and said patella retaining means has second disengagable fastening mean attached thereto for engaging said first fastening means and holding said patella retaining means in a desired location around said opening.

6. A musculoskeletal knee support as claimed in claim 1, wherein said flexible resilient material is an elastomeric foam backed with cloth fiber.

7. A musculoskeletal knee support as claimed in claim 1, wherein tightening means are provided adjacent at least one of said top and bottom edges for adjustably tightening the adjacent portion of said sleeve after said sleeve is placed over the, knee.

8. A musculoskeletal knee support as claimed in claim 2, wherein tightening means are provided adjacent at least one of said top and bottom edges for adjustably tightening the adjacent portion of said sleeve after said sleeve is placed over the knee.

9. A musculoskeletal knee support as claimed in claim 3, wherein tightening means are provided adjacent at least one of said top and bottom edges for adjustably tightening the adjacent portion of said sleeve after said sleeve is placed over the knee.

10. A musculoskeletal knee support as claimed in claim 1, wherein said sleeve has stiffening means attached approximately along a vertical medial line at each side of the knee.

11. A musculoskeletal knee support as claimed in claim 2, wherein said sleeve has stiffening means attached approximately along a vertical medial line at each side of the knee.

12. A musculoskeletal knee support as claimed in claim 3, wherein said sleeve has stiffening means attached approximately along a vertical medial line at each side of the knee.

13. A musculoskeletal knee support as claimed in claim 1, wherein said first and second stitched seams are respectively positioned approximately along the line of the fibular collateral ligament and the tibular collateral ligament.

14. A musculoskeletal knee support as claimed in claim 3, wherein said sleeve has tightening means adjacent at least one of said top and bottom edges for adjustably tightening the adjacent portion of said sleeve after the sleeve is placed over the knee and wherein said sleeve has stiffening means attached approximately along a vertical medial line at each side of the knee.

15. A musculoskeletal knee support as claimed in claim 1, 2, 3 or 10 wherein said generally horizontal aperture has a vertical width of between one fourth and one and one half inches.

* * * * *